(12) United States Patent
Halstrom et al.

(10) Patent No.: US 7,832,403 B2
(45) Date of Patent: *Nov. 16, 2010

(54) MANDIBLE POSITIONING DEVICES

(75) Inventors: Leonard W. Halstrom, Lions Bay (CA); Elias G. Diacopoulos, Export, PA (US)

(73) Assignee: Respironics, Inc., Murrysville, PA (US)

( * ) Notice: Subject to any disclaimer, the term of this patent is extended or adjusted under 35 U.S.C. 154(b) by 656 days.

This patent is subject to a terminal disclaimer.

(21) Appl. No.: 11/724,679

(22) Filed: Mar. 15, 2007

(65) Prior Publication Data

US 2007/0209666 A1  Sep. 13, 2007

Related U.S. Application Data

(63) Continuation-in-part of application No. 10/635,483, filed on Aug. 7, 2003, now Pat. No. 7,448,388.

(51) Int. Cl.
*A61F 5/56* (2006.01)
(52) U.S. Cl. ..................................... 128/848
(58) Field of Classification Search ................. 128/848, 128/859, 861, 862; 602/902; 433/6
See application file for complete search history.

(56) References Cited

U.S. PATENT DOCUMENTS

| | | | |
|---|---|---|---|
| 4,602,905 A | 7/1986 | O'Keefe, III | |
| 5,090,901 A | 2/1992 | Levandoski | |
| 5,154,609 A * | 10/1992 | George | ........................ 433/68 |
| 5,188,529 A * | 2/1993 | Luth | ........................... 433/68 |
| 5,409,017 A | 4/1995 | Lowe | |
| 5,683,244 A | 11/1997 | Truax | |
| 5,816,799 A | 10/1998 | Parker | |
| 5,826,579 A | 10/1998 | Remmers et al. | |
| 5,921,942 A | 7/1999 | Remmers et al. | |
| 6,012,920 A | 1/2000 | Woo | |
| 6,109,265 A | 8/2000 | Frantz et al. | |
| 6,255,262 B1 | 7/2001 | Keenan et al. | |
| 6,273,859 B1 | 8/2001 | Remmers et al. | |
| 6,286,508 B1 | 9/2001 | Remmers et al. | |
| 7,448,388 B2 * | 11/2008 | Halstrom | .................... 128/861 |

OTHER PUBLICATIONS

Lowe, "Dental Appliances for the Treatment of Snoring and obstructive Sleep Apnea:,Chapter 69, pp. 772-725 of Principles and Practice of Sleep Medicine" by W.B. Saunders, 1994.

* cited by examiner

*Primary Examiner*—Patricia M Bianco
*Assistant Examiner*—Camtu T Nguyen

(57) ABSTRACT

A pharyngeal airway adjuster, or mandible positioning device, has a maxillary dentition engagement component and a mandibular dentition engagement component, each on opposite sides of a plane extending therebetween. An adjustable connection couples the maxillary dentition engagement component with the mandibular dentition engagement component. The adjustable connection has a first adjustment screw having a longitudinal axis parallel to the plane and a second adjustment screw having a longitudinal axis perpendicular to the plane. The first and second adjustable screws are independently adjustable and structured to effect horizontal and vertical displacement, respectively, of the maxillary dentition engagement component relative to the mandibular dentition engagement component. The pharyngeal airway adjuster has a number of indicators adapted to indicate the amount of forwardly and rearwardly displacement effected by the first adjustment screw and/or the amount of upwardly and downwardly displacement effected by the second adjustment screw.

5 Claims, 5 Drawing Sheets

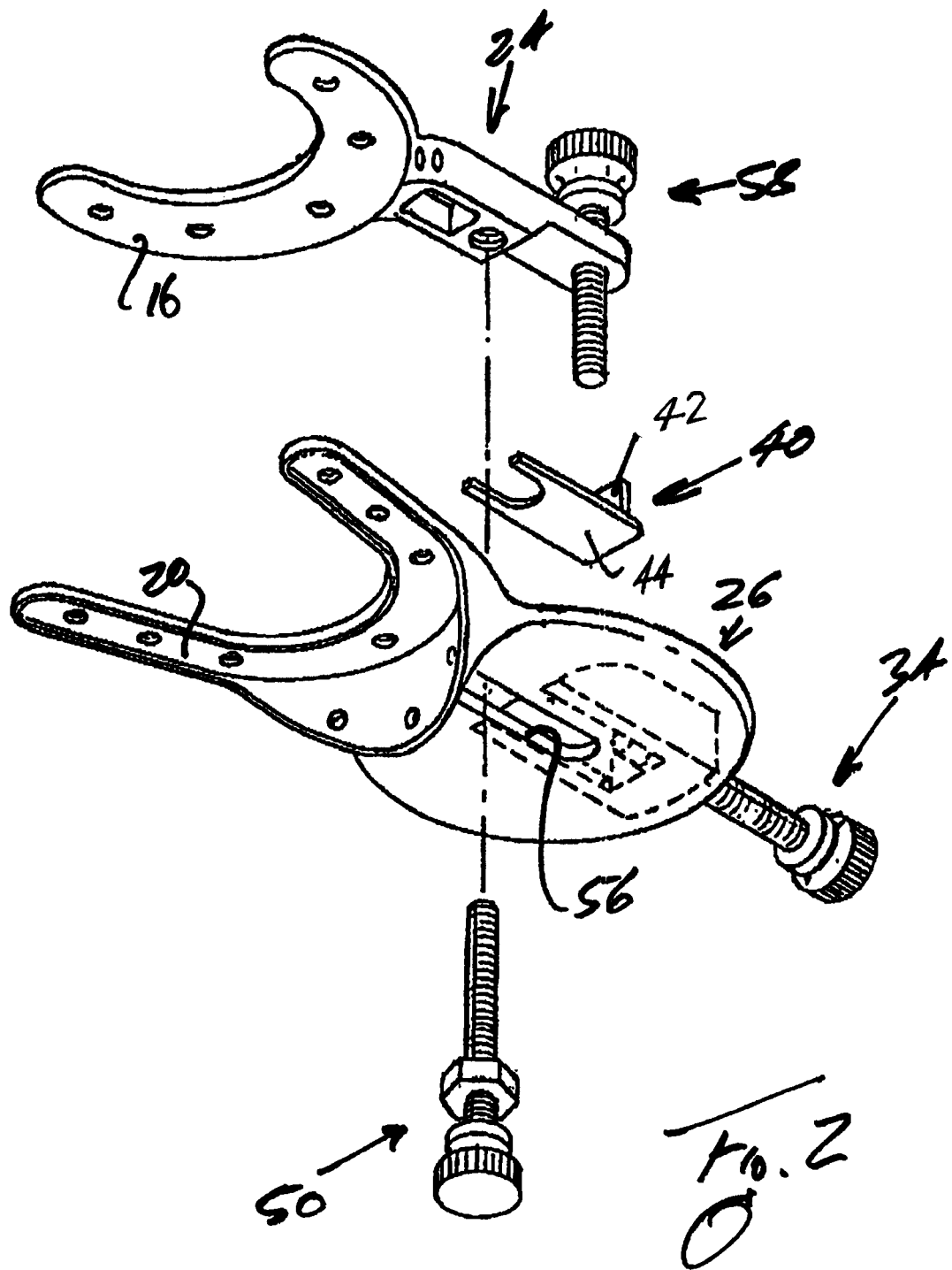

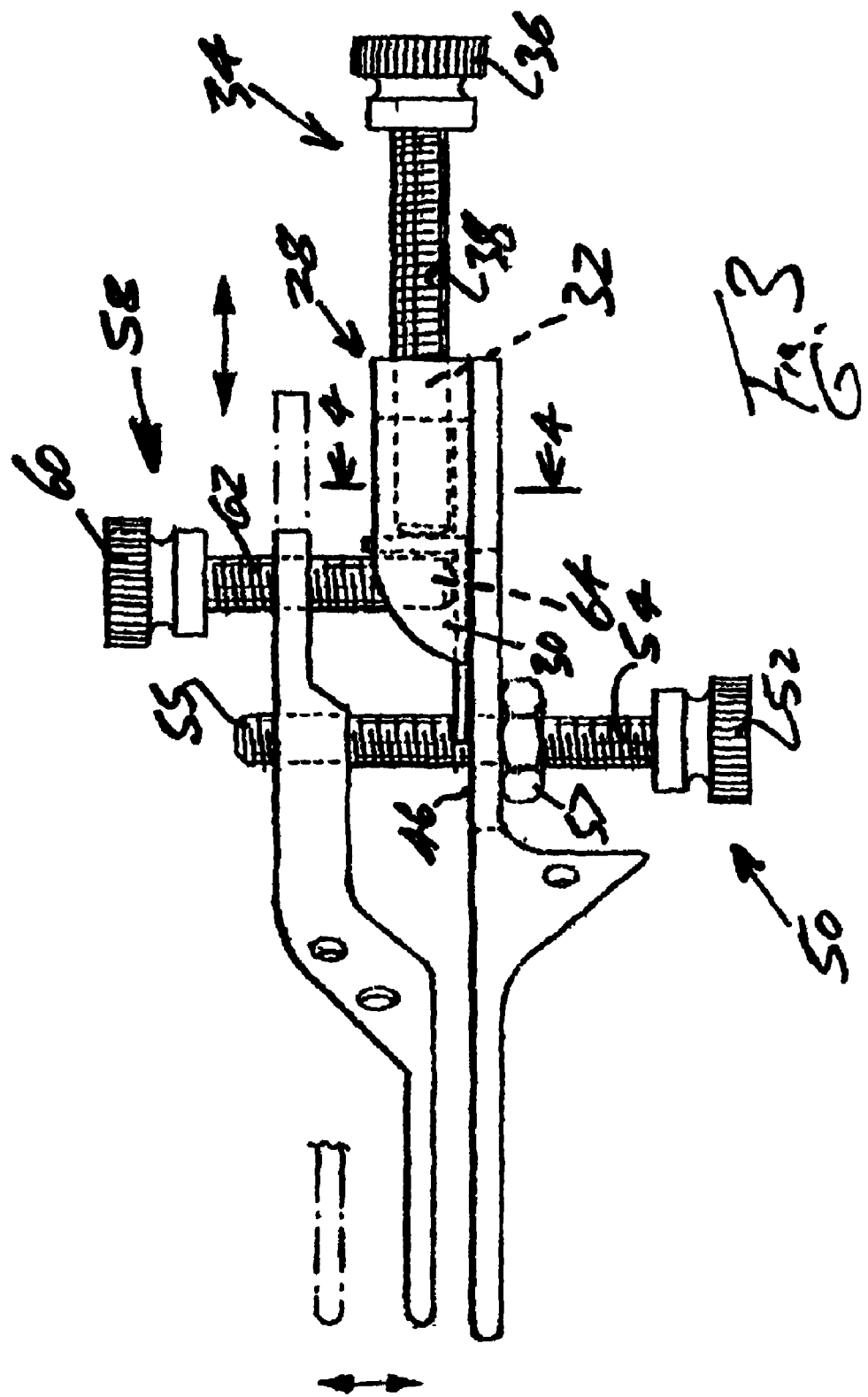

MANDIBLE POSITIONING DEVICES

CROSS-REFERENCE TO RELATED APPLICATIONS

This application is a continuation-in-part of U.S. patent application Ser. No. 10/635,483 filed 7 Aug. 2003, now U.S. Pat. No. 7,448,388, the contents of which are incorporated herein by reference.

BACKGROUND OF THE INVENTION

1. Field of the Invention

The present invention relates to mandible positioning devices for use as pharyngeal airway adjusters.

2. Description of the Related Art

In patients who are suffering from the sleep disorder known as obstructive sleep apnea, the flesh and muscles of the tongue and throat relax, as the patients attempt to sleep, so that the pharyngeal airway is blocked and, consequently, the patients briefly stop breathing. When this occurs, the patients are awakened by the consequent lack of oxygen and blood, which often occurs with a loud snort or a bodily jerk.

For the proper diagnosis and treatment of patients subject to sleep apnea, polysomnographic testing of the patients is performed in sleep centers or in the patients' homes, while the patients are asleep, to record various factors, including the oxygen level in the patients' blood, the heart action, chest and abdominal movements, and brain activity of the patients.

It has previously been proposed to provide a dental device for adjustably displacing the mandible of a patient horizontally and vertically, relative to the maxillary dentition of the patient, in order to thereby increase the pharyngeal airway size of the patient so as to counteract such blockage as caused in the above-described manner.

It has been found that the displacement of the mandible in a forward, i.e. horizontal, direction relative to the maxillary dentition and, also, in a downward, i.e. vertical, direction away from the maxillary dentition should be adjusted, while the patient is being tested, in order to determine the optimum positioning of the mandible.

In U.S. Pat. No. 5,409,017, issued Apr. 25, 1995, to Lowe, there is disclosed a mandible positioning device having upper and lower bite blocks, which fit onto and engage the maxillary and mandibular dentition of a patient, with an adjustable connection between the upper and lower bite blocks. This connection allows the position of the lower bite block to be adjusted forwardly and rearwardly, i.e. horizontally, relative to the upper bite block, in order to thereby adjust the relative positions of the upper and lower bite blocks and to adjust correspondingly the position of the patient's mandible.

It is, however, a disadvantage of this prior device that the connection is located between the upper and lower bite blocks and, therefore, is not accessible while the device is installed in the mouth of a patient. In order to adjust the device, it is necessary to withdraw the device from the patient's mouth.

A further disadvantage of this prior device is that it does not allow the spacing between the upper and lower bite blocks to be adjusted.

SUMMARY OF THE INVENTION

It is accordingly an object of the present invention to provide a novel and improved mandible positioning device having upper and lower bite blocks which can be manually adjusted in position relative to one another while the device is installed in the mouth of a patient.

It is a further object of the present invention to provide a manually adjustable mandible positioning device which allows a lower bite block to be adjusted forwardly relative to an upper bite block and which also allows the vertical spacing between the upper and lower bite blocks to be adjusted.

According to the present invention, there is provided a mandible positioning device comprising upper and lower bite blocks and a manually adjustable connection interconnecting the upper and lower bite blocks for displacing the upper and lower bite block relative to one another, the manually adjustable connection protruding forwardly from the upper and lower bite blocks so that, in use of the mandible positioning device, the manually adjustable connection is located forwardly from the dentition of a patient fitted with the mandible positioning device. The manually adjustable connection can therefore be adjusted while the device remains in the mouth of a patient.

Consequently, when the present mandible positioning device is in use, the position of the lower bite block can be adjusted, for example in a clinical setting while the patient is awake and in order to allow visual inspection of the patient's airway, e.g. to determine the optimum relative positions of the upper and lower bite blocks to counteract snoring. By locating the manually adjustable connection forwardly of the upper and lower bite blocks, the space between the upper and lower bite blocks, within the patient's mouth, can be left unobstructed by these members, which facilitates such visual inspection.

Another use of the present invention is to enable relative adjustment of the upper and lower bite blocks while the patient fitted with the device according to the present invention is unconscious, e.g. in a post-operative state, or otherwise incapacitated, in order to contract sleep apnea.

The manually adjustable connection may comprise a pair of independently manually adjustable members controlling, respectively, forward or horizontal displacement of the lower bite block and the spacing, or vertical spacing, between the upper and lower bite blocks The pair of manually adjustable members preferably comprises a first adjustment screw having a longitudinal axis extending forwardly from the mandible positioning device for horizontal adjustment, and a second adjustment screw, having a longitudinal axis perpendicular to the longitudinal axis of the first-mentioned adjustment screw, for vertical adjustment.

BRIEF DESCRIPTION OF THE DRAWINGS

The invention will be more readily understood from the following description of a preferred embodiment thereof, given by way of example, with reference to the accompanying drawings, in which:

FIG. 2 shows an exploded view, taken in perspective from below, of components of the device of FIG. 1;

FIG. 3 shows a view, taken in side elevation, of the device of FIG. 1.

DETAILED DESCRIPTION OF THE EXEMPLARY EMBODIMENTS

As employed herein, the term "number" shall mean one or more than one and the singular form of "a", "an", and "the" include plural referents unless the context clearly indicates otherwise.

As employed herein, the statement that two or more parts are "connected" or "coupled" together shall mean that the parts are joined together either directly or joined together through one or more intermediate parts. Further, as employed herein, the statement that two or more parts are "attached" shall mean that the parts are joined together directly.

Figure 1:
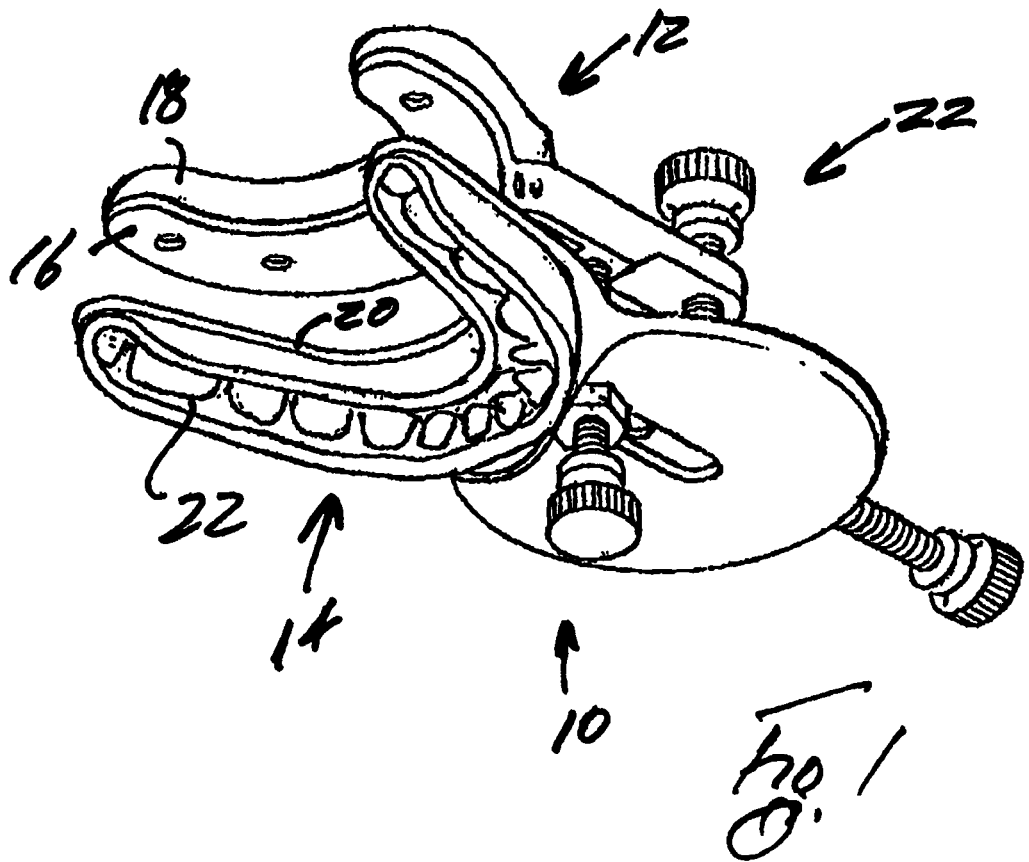
FIG. 1 shows a view, taken in perspective from below, of a mandible positioning device embodying the present invention.

The mandible positioning device (also referred to herein as a pharyngeal airway adapter) shown in FIG. 1 is indicated generally by reference numeral 10 and comprises a maxillary dentition engagement component or upper bite block indicated generally by reference numeral 12 and a mandibular dentition engagement component or lower bite block indicated generally by reference numeral 14.

More particularly, the upper bite block 12 comprises a flat U-shape plate or tray 16 with a dental molding 18, shaped to interfit with the maxillary dentition of a patient, and the lower bite block comprises a U-shaped inverted tray 20 carrying, at its underside, a dental molding 22 shaped for interengagement with the mandibular dentition of the patient.

The upper bite block 12 is coupled with the lower bite block 14 by an adjustable connection, indicated generally by reference numeral 22, which projects forwardly from the upper and lower bite blocks 12 and 14 so as to protrude beyond the mouth and lips of a patient (not shown). The adjustable connection 22 is therefore accessible at the exterior of the patient's mouth while the device remains fitted to the patient with the upper and lower bite blocks 12 and 14 in engagement with the patient's dentition. In the current embodiment, the adjustable connection 22 is adjusted manually.

The adjustable connection 22 includes a projection, indicated generally by reference numeral 24 in FIG. 2, which protrudes forwardly from the upper bite block tray 16, and a disc-shaped projection, indicated generally by reference numeral 26, which protrudes forwardly from the lower bite block tray 20. It is contemplated that the shape of projection 24 and disc-shaped projection 24 may be altered while remaining within the scope of the present invention.

The disc-shaped projection 26 is formed, on its upper surface, with an upwardly-open formation, indicated generally by reference numeral 28 in FIG. 3. The formation 28 has parallel side walls 30 and, at the forward end of the formation 28, an end wall 32 extending between the side walls 30.

A first manually adjustable member or adjustment screw, indicated generally by reference numeral 34, has a knurled head 36 and a threaded shank 38. The threaded shank 38 extends though and is in threaded engagement with an opening in the end wall 32 of the formation 28, with the longitudinal axis of the shank 38 extending in a posterior and anterior direction of the device 10. As will be discussed in more detail, the first adjustment screw 34 is structured to effect displacement of the upper bite block 12 forwardly and rearwardly relative to the lower bite block 14.

The rear end of the shank 38, opposite from the knurled head 36, abuts a slide member, which is indicated generally by reference numeral 40 in FIG. 2.

The slide member 40 comprises a vertical end flange 42, extending vertically upwardly from a horizontal slide plate 44.

Figure 4:
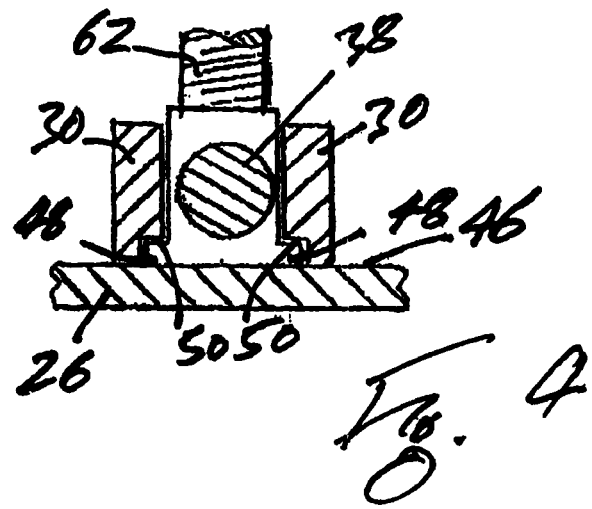
FIG. 4 shows a broken-away view, taken in cross-section along the line 4-4 of FIG. 3.

The slide plate 44 is slidably supported on an upper surface 46 of the disc-shaped projection 26 and, as shown in FIG. 4, has opposite longitudinal marginal end portions 48 engaged in recesses 50 formed in opposed faces of the side walls 30 adjacent the upper surface 46 of the disc-shaped projection 26.

The upper and lower projections 24 and 26 are coupled by a second manually adjustable member or adjustment screw, which is indicated generally by reference numeral 50 in FIG. 3 and which has a vertical longitudinal axis extending perpendicular to the horizontal longitudinal axis of the first adjustment screw 34.

The second adjustment screw 50 has a knurled head 52 and a shank 54 which extends upwardly from the head 52 through a slot 56 in the disc-shaped projection 26, the shank 54 having an upper end 55 which extends though (in an upward/downward direction) and is in threaded engagement with an opening in the upper projection 24. A nut 57 on the shank 54 of the second adjustment screw 50 underlies the disc-shaped projection 26. As will be discussed in more detail, the second adjustment screw 50 is structured to effect displacement of the upper bite block 12 upwardly and downwardly relative to the lower bite block 14.

A third manually adjustable member or adjustment screw, indicated generally by reference numeral 58, has a knurled head 60 and a shank 62 extending downwardly from the knurled head 60, the shank 62 being parallel to the shank 54 of the second adjustment screw 50 and, thus, having a longitudinal axis perpendicular to that of the first adjustment screw 34.

A lower end 64 of the shank 62 of the adjustment screw 58 abuts the upper surface of the slide plate 46 of the slide member 40.

By rotation of the first adjustment screw 34 relative to the formation 28, the slide member 40 can be urged to the left, as viewed in FIG. 3, relative to the formation 28. The slide plate 44 of the slide member is thereby pressed against the shank 62 of screw 58, so that the formation 28 and, therewith, the disc-shaped projection 26 and the lower bite block 14 are displaced to the right, as viewed in FIG. 3, relative to the adjustment screw 58, the upper projection 24, and the upper bite block 12.

During this displacement, the shank 54 of the second adjustment screw 50 is correspondingly displaced along the slot 56 formed in the disc-shaped projection 26.

In this way, the lower bite block 14 can be adjustably displaced relative to the upper bite block 12 in a forward or horizontal direction, parallel to a horizontal plane between the upper and lower bite blocks 12 and 14.

To adjustably increase the vertical spacing of the upper and lower bite blocks 12 and 14, the nut 57 is firstly loosened from the disc-shaped projection 26, and the second adjustment screw 50 is then rotated to permit corresponding displacement of the disc-shaped lower projection 26 and, therewith, the lower bite block 14 downwardly relative to the upper projection 24 and the upper bite block 12 and perpendicular to the above-mentioned horizontal plane.

When this vertical displacement has been completed, to an extent which is determined by the position of the nut 57 along the shank 54 of the second adjustment screw 50, the adjustment screw 58 is rotated to press downwardly onto the slide member 46 and, thereby, to press the disc-shaped lower projection 26 against the nut 57.

The first and second adjustment screws 34 and 58 are thus adjustable independently of one another for adjusting the forward displacement and the vertical spacing, respectively; of the lower bite block 14 relative to the upper bite block 12.

The mandible positioning device may incorporate a number of indicators thereon which are adapted to indicate the amount of horizontal and/or vertical adjustment that has been effected by the adjustment screws. The indicators may also be employed to indicate the horizontal positioning and/or vertical positioning of the upper bite block 12 relative to the lower bite block 14. The number of indicators may be used to determine the amount that a patient's mandible has moved (horizontally and/or vertically) relative to the patient's maxilla, thus adding the clinician in finding the optimum positioning of the mandible during testing.

Figure 5:
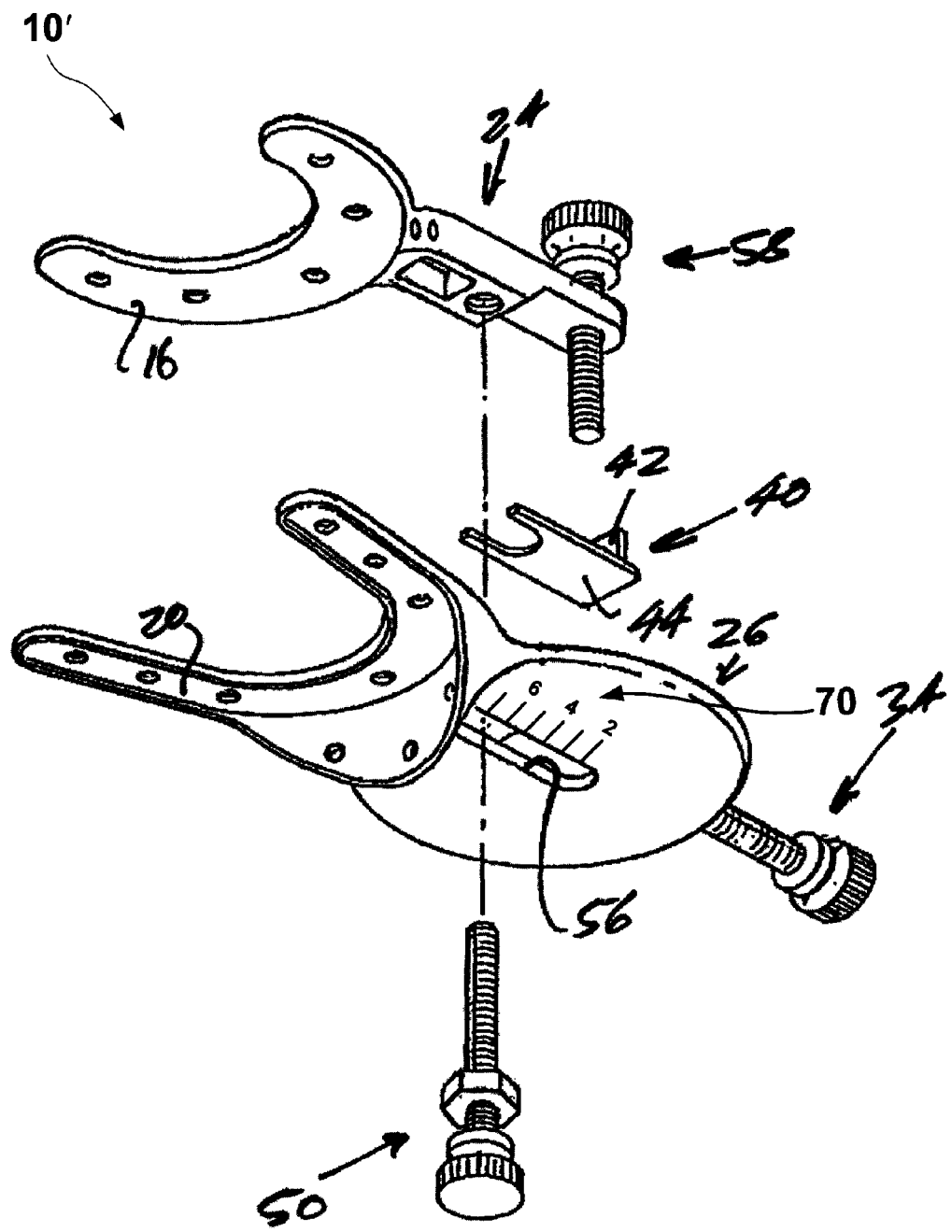
FIG. 5 shows an exploded view, taken in perspective from below, of components of another embodiment of a mandible positioning device embodying the present invention.
Figure 6:
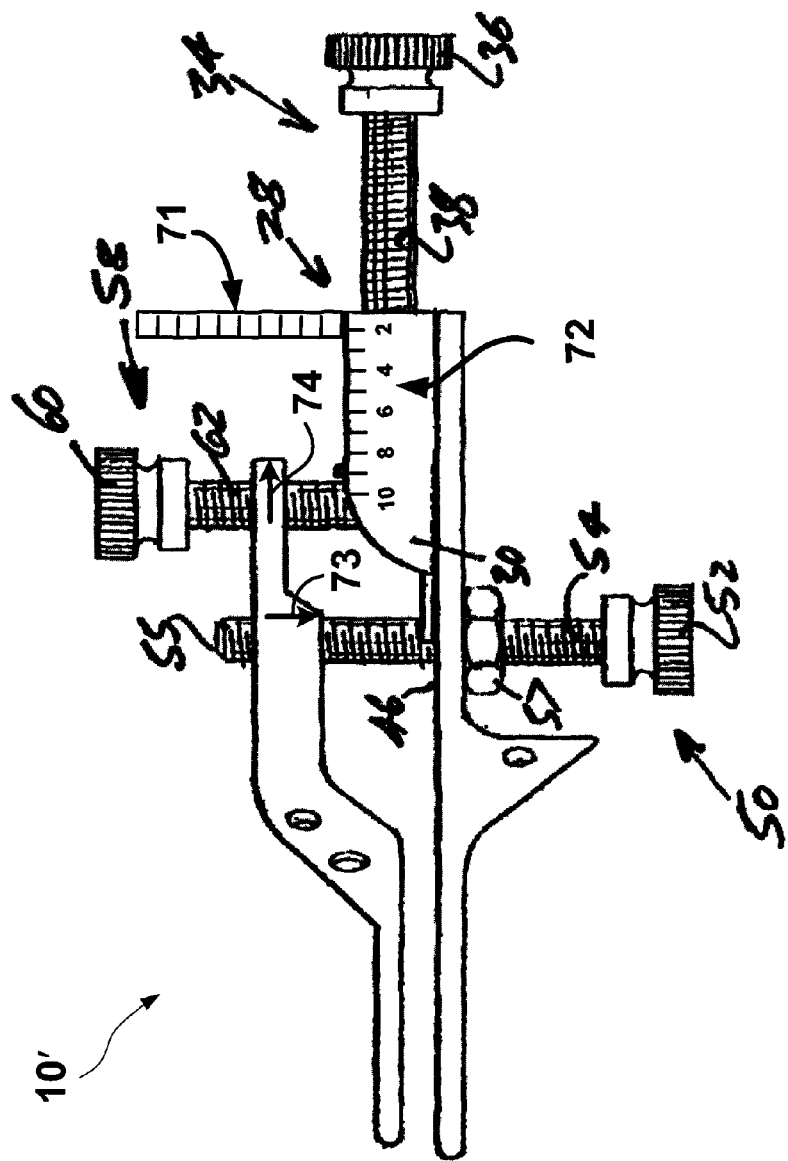
FIG. 6 shows a view, taken in side elevation, of the device depicted in FIG. 5.

FIGS. 5 and 6 illustrate one such mandible positioning device 10' according to one embodiment. As shown in FIGS. 5 and 6, the number of indicators include a graduated scale 70 located on the bottom surface of the disc-shaped projection 26, a graduated scale 72 located on side wall 30, and a graduated scale 71 extending from formation 28. In the current embodiment, the graduations are spaced one (1) millimeter apart, although other distances may be employed while remaining within the scope of the present invention. Although illustrated as including two graduated scales (i.e., 70, 72) for measuring horizontal adjustment and one graduated scale (i.e., 71) for measuring vertical adjustment, any number of scales and/or other indicators may be employed to measure the amount of horizontal and/or vertical adjustment while remaining within the scope of the present invention.

Generally, mandible positioning device 10' is zeroed horizontally by rotating the first adjustment screw 34 relative to the formation 28 such that slide member 40 is urged to its right most (as viewed in FIG. 3) limit of travel relative to the formation 28 (i.e., the disc-shaped projection 26 and the lower bite block 14 are urged to its left most limit of travel relative to the upper bite block 12). Mandible positioning device 10' is zeroed vertically by rotating the second adjustment screw 50 and the third adjustment screw 58 such that the upper bite block 12 moves downwardly and/or lower bite block 14 moves upwardly (as viewed in FIG. 3) such that upper bite block 12 and lower bite block 14 abut one another.

Once zeroed, the mandible positioning device 10' is adjusted as previously discussed until the desired amount of horizontal and vertical movement has be applied. By comparing the location of shank 54 of the second adjustment screw 54 relative to the graduated scale 70, the amount of horizontal adjustment effected by first adjustment screw 34 may be determined. Alternatively, the amount of horizontal adjustment effected by first adjustment screw 34 may be determined by comparing the location of shank 62 of the third adjustment screw 58 relative to the graduated scale 72. The amount of vertical adjustment effected by second adjustment screw 50 and/or third adjustment screw 58 may be determined using graduated scale 71 in conjunction with indicator arrow 74.

It should be noted that other devices and or methods may be used to determine the amount of horizontal and/or vertical adjustment. Additionally, it is contemplated that the method of zeroing the mandible positioning device 10' may be altered while remaining within the scope of the present invention. For example, the mandible positioning device 10' may zeroed relative to the dentition of the particular patient being tested. The amount of horizontal and/or vertical adjustment applied thereafter is determined from this "floating zero" point.

As will be apparent to those skilled in there are various modifications may be made in the above-described embodiment of the present invention within the scope of the appended claims. For example, while the above-described embodiment of the invention employs adjustment screws for adjusting the relative positions of the upper and lower bite blocks 12 and 14, it is envisaged that other means, for example spring-actuated detents, could be employed for this purpose.

What is claimed is:

1. A pharyngeal airway adjuster, comprising:
    (a) a maxillary dentition engagement component;
    (b) a mandibular dentition engagement component, wherein the maxillary dentition engagement component and the mandibular dentition engagement component are disposed on opposite sides of a plane extending therebetween; and
    (c) an adjustable connection coupling the maxillary dentition engagement component and the mandibular dentition engagement component, wherein the adjustable connection comprises:
        (1) a first adjustment screw having a longitudinal axis parallel to the plane,
        (2) a second adjustment screw having a longitudinal axis perpendicular to the plane, wherein manipulation of the first and the second adjustment screws displaces the maxillary dentition engagement component relative to the mandibular dentition engagement component, wherein the adjustable connection protrudes forwardly from the maxillary dentition engagement component and the mandibular dentition engagement component so that, in use of the pharyngeal airway adjuster, the adjustable connection is located in front of and external to a patient fitted with the pharyngeal airway adjuster so as to be accessible at an exterior of such a patient's mouth when the pharyngeal airway adjuster is in use, wherein the first adjustment screw controls displacement of the mandibular dentition engagement component forwardly relative to the maxillary dentition engagement component, wherein the second adjustment screw controls displacement of the maxillary dentition engagement component and the mandibular dentition engagement component towards and away from one another,
        (3) a first forward projection extending from the maxillary dentition engagement component and having a longitudinal axis extending forwardly from the maxillary dentition engagement component,
        (4) a second forward projection extending from the mandibular dentition engagement component, and wherein the second adjustment screw has a longitudinal axis perpendicular to a longitudinal axis of the first adjustment screw, and
        (5) a number of indicators adapted to indicate at least one of:
            (i) an amount of horizontal adjustment effected by the first adjustment screw, and
            (ii) an amount of vertical adjustment effected by the second adjustment screw.

2. A pharyngeal airway adjuster as claimed in claim 1, wherein the mandibular dentition engagement component has a slot extending parallel to the first-mentioned adjustment screw and the second adjustment screw extends though the slot into threaded engagement with the maxillary dentition engagement component.

3. A pharyngeal airway adjuster as claimed in claim 1, wherein the first adjustment screw and the second adjustment screw are adjustable independently of one another for displacing the maxillary dentition engagement component and the mandibular dentition engagement component parallel to the plane and perpendicular to the plane, respectively.

4. A pharyngeal airway adjuster as claimed in claim 1, wherein at least some of the number of indicators include a graduated scale.

5. A pharyngeal airway adjuster as claimed in claim 1, further comprising:

a third screw having a longitudinal axis parallel to the longitudinal axis of the second adjustment screw; and a locknut associated with at least one of the second adjustment screw and the third adjustment screw.

* * * * *